(12) United States Patent
Sohn et al.

(10) Patent No.: US 6,867,316 B2
(45) Date of Patent: Mar. 15, 2005

(54) PLATINUM(II) COMPLEXES OF N-SUBSTITUTED AMINO DICARBOXYLATES AND THE PREPARATION METHOD THEREOF

(75) Inventors: Youn Soo Sohn, Seoul (KR); Yeong-Sang Kim, Seoul (KR); Rita Song, Seoul (KR)

(73) Assignee: Board of Trustees, Ewha Womans University, Seoul (KR)

( * ) Notice: Subject to any disclaimer, the term of this patent is extended or adjusted under 35 U.S.C. 154(b) by 0 days.

(21) Appl. No.: 10/752,566

(22) Filed: Jan. 8, 2004

(65) Prior Publication Data

US 2004/0162342 A1 Aug. 19, 2004

(30) Foreign Application Priority Data

Feb. 19, 2003 (KR) .................. 10-2003-0010492

(51) Int. Cl.$^7$ ...................... C07F 15/00; A61K 31/28
(52) U.S. Cl. ....................... 556/137; 514/492
(58) Field of Search ................. 556/137; 514/492

(56) References Cited

U.S. PATENT DOCUMENTS

| | | | | |
|---|---|---|---|---|
| 4,284,579 A | * | 8/1981 | Meischen et al. | ........ 556/19 |
| 4,895,936 A | * | 1/1990 | Talebian et al. | ........ 536/17.1 |
| 4,946,954 A | * | 8/1990 | Talebian et al. | ........ 536/121 |

OTHER PUBLICATIONS

D. Lebwohl et al., "Clinical Development of Platinum Complexes in Cancer Therapy: An Historical Perspective and an Update," European Journal of Cancer, vol. 34, No. 10, pp. 1522–1534, 1998.

E. Wong et al., "Current Status of Platinum–Based Antitumor Drugs," Chem. Rev., vol. 99, pp. 2451–2466, 1999.

O, Gandolfi et al., "Aminomalonato(1,2–Diaminocyclohexane)Platinum(II): A Competitive Antitumor Compound WithinH a New Class of Neutral, Chemically Stable, Water Soluble, Functionalized Platinum(II) Complexes," Iorganica Chimica Acta, 135, pp. 27–31, 1987.

J.D. Roberts et al., "Water Soluble DACH–PT(II) Complexes: Problems of Purification; Stability of Complexes with Nitrogen–Containing Ligands," Inorganica Chimica Acta, 153, pp. 123–127, 1988.

T.G. Appleton et al., "Reactions of the CIS–Diamminediaquaplatinum(II) Cation with 2–Aminomalonic and Acid and its Homologues, Aspartic and Glutamic Acids. Rearrangements of Metastable Complexes with Carboxylate–Bound Ligands to N,O–Chelates and Formation of DI– and Trinuclear Complexes$^1$," Inorg. Chem., 29, pp. 3985–3990, 1990.

Y.–A. Lee et al., Diaminoplatinum(II) Complexes of Glutamic Acid: Obvious.

Y.–A. Lee et al., "Linkage Isomerism Dependent on Solvent and Temperature. Synthesis and Stryctural Properties of Diamineplatinum(II) Complexes of Allyl– and Diallylmalonate Ligands," Inorg. Chem., 38, pp. 531–537, 1999.

O. Gandolfi et al., "Aminomalonato(1,2–Diaminocyclohexane)Platinum(II): A Competitive Antitumor Compound Within a New Class of Neutral, Chemically Stable, Water Soluble, Functionalized Platinum(II) Complexes," Inorganica Chimica Acta, 135, pp. 27–31, 1987.

S.S. Lee et al., "Cationic Diamineplatinum(II) Complexes of Nalidixic Acid," Inorganica Chimica Acta, 239, pp. 133–138, 1995.

\* cited by examiner

*Primary Examiner*—Porfirio Nazario-Gonzalez
(74) *Attorney, Agent, or Firm*—Morrison & Foerster LLP

(57) ABSTRACT

Disclosed are a platinum (II) complex of N-substituted amino dicarboxylate showing antitumor activity represented by the following formula (1) and a preparation method thereof:

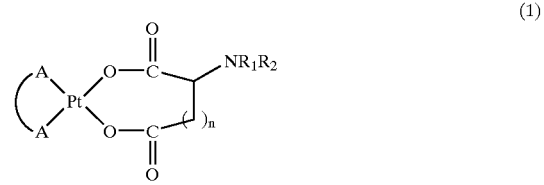

(1)

wherein n is 1 or 2; A—A is a diamine selected from the group consisting of trans-(±)-1,2-diaminocyclohexane, ethylenediamine and 2,2-dimethyl-1,3-propanediamine; and $R_1$ is hydrogen and $R_2$ is RCO or $RSO_2$, wherein R is an alkyl selected from the group consisting of methyl, ethyl, n-propyl, n-butyl and t-butyl or an aryl selected from the group consisting of phenyl and substituted phenyl group, or $R_1R_2$ is phthaloyl.

6 Claims, No Drawings

PLATINUM(II) COMPLEXES OF N-SUBSTITUTED AMINO DICARBOXYLATES AND THE PREPARATION METHOD THEREOF

BACKGROUND OF THE INVENTION

1. Field of the Invention

The present invention relates to a platinum(II) complex of N-substituted amino dicarboxylate showing anti-cancer activity, and to a preparation method thereof.

2. Description of the Background Art

Cisplatin, a platinum anti-tumor agent, is one of the most widely used anti-tumor agents in the world. Especially, it has been known that cisplatin shows superior antitumor activities against testicular cancer, ovarian cancer, bladder cancer, etc. However, cisplatin has been restricted in use due to its strong adverse effects for kidney, bone marrow and nervous system (D. Lebwohl, R. Canetta, *Eur. J. Cancer*, 34, 1522 (1998)).

Accordingly, a great deal of researches for the development of platinum complexes showing superior antitumor activities with lower toxicity have been actively performed worldwide. Especially, in order to improve solubility of the platinum complex in water and to reduce toxicity, dicarboxylate anions have been introduced into the platinum complex. As a result, carboplatin has been developed and presently used in clinic (E. Wong, C. M. Giandomenico, *Chem, Rev.*, 99, 2451 (1999)).

Recently, it has been reported that a platinum complex chelated by amino malonate which is a dicarboxylate having amino groups, shows superior anti-tumor activity (O, Gandolfi, H. C. Apfelbaum, J. Blum, Inorg. Chim. Acta, 135, 27 (1987)). This platinum complex is a (O,O)-chelate form in which the platinum atom is coordinated by two oxygen atoms of the dicarboxylate. However, the (O,O)-chelate form of the platinum complex has a problem because it is chemically unstable and thus, easily converted into a (N,O)-chelate form showing no antitumer activity in aqueous solution by a linkage isomerism as follows (J. D. Roberts, W. J. Schmidt, W. P. Tong, M. P. Hacker, Inorg. Chim. Acta, 153, 123 (1988)):

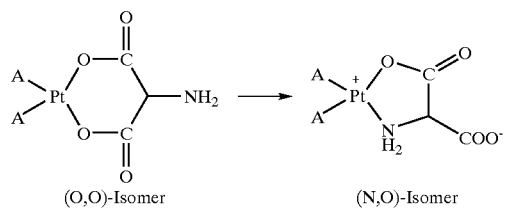

(O,O)-Isomer    (N,O)-Isomer

Such linkage isomerism takes place more readily in aqueous solution for the platinum complexes of amino dicarboxylates such as glutamate and aspartate, and therefore, it has been known that it is very difficult to synthesize a pure (O,O)-chelated complex having superior antitumer activity (T. G. Appleton, J. R. Hall, D. W. Neale, C. S. M. Thompson, *Inorg. Chem.*, 29, 3985 (1990); and Y.-A. Lee, J. Hong. O.-S. Jung, Y. S. Sohn, *Bull. Korean Chem. Soc.*, 15, 669 (1994)).

SUMMARY OF THE INVENTION

Therefore, an object of the present invention is to provide a platinum(II) complex of N-substituted amino dicarboxylate which is stable in an aqueous solution with no linkage isomerism and shows superior antitumor activity, and to provide a preparation method thereof.

To achieve the above and other objects of the invention, as embodied and broadly described herein, we have designed and synthesized a new class of platinum complexes employing amino dicarboxylates N-substituted with various stereo-specific substituents such as acyl group, tosyl group or phthaloyl group. We have discovered that the platinum complexes prepared by the above method are not only chemically stable in aqueous solution with no linkage isomerism, but also exhibit superior antitumor activity compared to the conventional platinum anti-tumor agents.

The foregoing and other objects, features, aspects and advantages of the present invention will become more apparent from the following detailed description of the invention.

DETAILED DESCRIPTION OF THE PREFERRED EMBODIMENTS

The conventional platinum complexes of amino dicarboxylates are disadvantageous in that they are easily dissolved in water due to their high hydrophilicity, but their bioavailability is low due to their low lipophilicity.

On the contrary, it was discovered that the platinum complexes having a lipophilic substituent on the N-position of the amino dicarboxylate ligand are relatively less soluble in water, but since they are more lipophilic, they can be formulated with a lipophilic drug delivery material such as liposome, so that its bioavailability can be improved greatly.

Therefore, the present invention relates to a platinum(II) complex of the N-substituted amino dicarboxylate showing antitumor activity, which is represented by the following chemical formula (1):

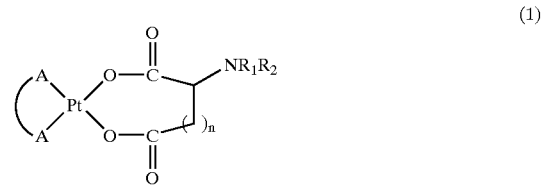

(1)

wherein n is 1 or 2;

A—A is diamine selected from the group consisting of trans-(±)-1,2-diaminocyclohexane (dach), ethylenediamine (en) and 2,2-dimethyl-1,3-propanediamine (dmpda); and $R_1$ is hydrogen and $R_2$ is RCO or $RSO_2$, wherein R is an alkyl selected from the group consisting of methyl, ethyl, n-propyl, n-butyl and t-butyl or an aryl selected from the group consisting of phenyl and substituted phenyl group, or $R_1R_2$ is a phthaloyl group.

The present invention also relates to a preparation method of the platinum(II) complex of N-substituted amino dicarboxylate represented by the chemical formula (1).

The compound of the chemical formula (1) can be prepared by the method comprising the steps of (a) preparing a metal salt of N-substituted amino dicarboxylate from an amino dicarboxylic acid or its ester, and (b) reacting the metal salt prepared in step (a) with a (diamine)platinum(II) sulfate complex. The metal salt of N-substituted amino dicarboxylate may be a barium salt or a sodium salt, but it is not limited thereto.

When the platinum(II) complex of the N-substituted amino dicarboxylate represented by the chemical formula (1) is synthesized using a barium salt, it can be prepared in the following manner:

First, a barium salt of N-substituted amino dicarboxylate represented by the chemical formula (2) is prepared according to a known method in the art (e.g., Y.-A. Lee, Y. K. Chung, Y. S. Sohn, *Inorg, Chem.,* 38, 531 (1999)).

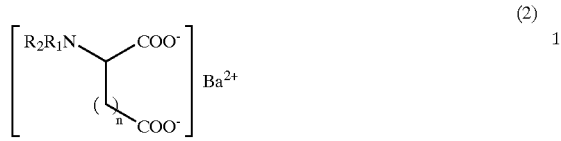

(2)

wherein $R_1$ and $R_2$ are the same as defined in chemical formula (1).

The barium salt represented by the chemical formula (2) is then reacted with a platinum(II) sulfate complex represented by the chemical formula (3) which can be prepared according to a known method (O. Gandolfi, H. C. Apfelbaum and J. Blum, *Inorg. Chim. Acta,* 135, 27 (1987)), in a manner as shown in the reaction scheme (1), to obtain the platinum(II) complex of N-substituted amino dicarboxylate.

cis-[Pt(A)$_2$(SO$_4$)]  (3)

Reaction Scheme (1):

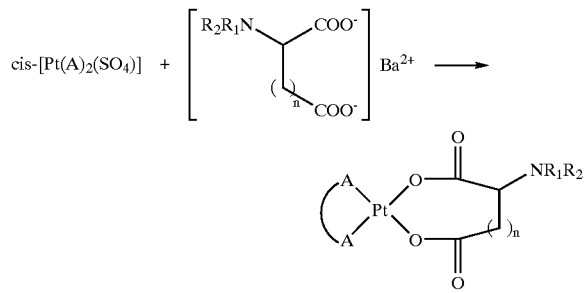

In the above chemical formula (3) and reaction scheme (1), n, A-A, $R_1$ and $R_2$ are the same as defined in chemical formula (1).

However, if the solubility of the platinum complex of N-substituted amino dicarboxylate finally obtained is low in water, as in the case that $R_2$ is a lipophilic substituent such as carbobenzyloxy group, a sodium salt of the N-substituted amino dicarboxylate represented by the chemical formula (4) is reacted with a platinum(II) sulfate complex of formula (3), in a manner as shown in the reaction scheme (2), to obtain the platinum(II) complex of N-substituted amino dicarboxylate.

(4)

Reaction Scheme (2):

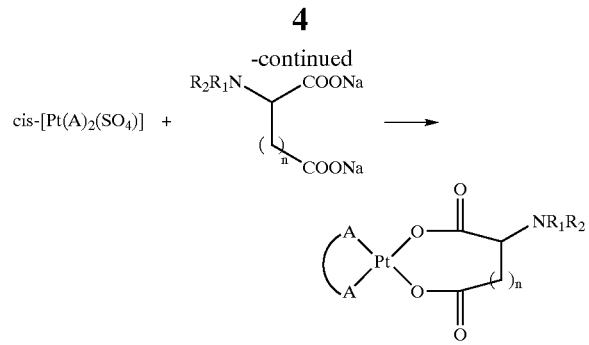

In the above formula (4) and reaction scheme (2), n, A-A, $R_1$ and $R_2$ are the same as defined in chemical formula (1).

Meanwhile, the reactions as shown in the above reaction schemes 1 and 2 are preferably performed in an aqueous solution at room temperature. Molar ratio of the salt of the N-substituted amino dicarboxylate to platinum(II) sulfate complex is preferably in the range of 1.0:1.0–1.3.

It was discovered from the nuclear magnetic resonance spectrum that since the (O,O)-isomer was chemically stabilized, the (N,O)-isomer was not generated from the platinum(II) complex of N-substituted amino dicarboxylate of the chemical formula (1). In addition, it was also discovered that not only the platinum(II) complex of N-substituted amino dicarboxylate of the chemical formula (1) shows higher antitumor activity, but also its physico-chemical properties and antitumor activity are reproducibile.

EXAMPLES

Hereinafter, the present invention will be described in more detail with reference to the following examples and embodiments, but the present invention is not limited thereto.

In the following examples, elemental analysis of carbon, hydrogen and nitrogen for the compound of the present invention was performed using Perkin-Elmer C, H and N analyzer. Hydrogen and platinum nuclear magnetic resonance spectra were respectively measured using Bruker DPX-250 NMR and Varian Gemini-300 NMR spectrometers, and infrared absorption spectra were measured using Nicolet Impact 400 RF-IR spectrometer.

Example 1

Preparation of (N-acetyl-L-glutamato-O,O)(trans-(±)-1,2-diaminocyclo-hexane-N,N)platinum(II) complex, [Pt(dach)(AcGlu)]

An aqueous solution of (trans-(±)-1,2-diaminocyclohexane-N,N)platinum(II) sulfate (Pt(dach)SO$_4$.H$_2$O, 0.42 g) in 20 ml of water was added to an aqueous solution of barium salt of N-acetyl-L-glutamic acid (Ba (AcGlu).2H$_2$O, 0.36 g) in 20 ml of water. The resulting solution was stirred at room temperature for 3 hours. After BaSO$_4$ precipitated was removed by filtering, the filtrate was then freeze-dried, and the solid product was recrystallized from water and acetone, to obtain the desired product in 85% yield.

Composition: C$_{13}$H$_{23}$N$_3$O$_5$Pt.2H$_2$O.

Elemental Analysis: C, 29.15; H, 5.07; N, 7.82; theoretical value: C, 29.32; H, 5.11; N, 7.89.

H-NMR spectra (D$_2$O, ppm): 4.0 (m, 1H, Glu-CH), 2.3–2.1 (m, 4H, dach-CH$_2$, Glu-CH$_2$), 2.0–1.7 (m, 7H, Ac—CH$_3$, dach-CH, Glu-CH$_2$), 1.5–1.4 (m, 2H, dach-CH), 1.3–1.0 (m, 4H, dach-CH).

Pt-NMR spectrum (D$_2$O, ppm): −1864.4.

IR absorption spectrum (KBr, cm$^{-1}$): 3232w, 3098w, 1631s, 1555m, 1383m.

Example 2

Preparation of (N-propionyl-L-glutamato-O,O) (trans-(±)-1,2-diaminocyclo-exane-N,N)platinum (II), [Pt(dach)(ProGlu)]

An aqueous solution of (trans-(±)-1,2-diaminocyclohexane-N,N)platinum(II) sulfate (Pt(dach) SO$_4$.H$_2$O, 0.85 g) in 25 ml of water was add to an aqueous solution of barium salt of N-propionyl-L-glutamic acid (Ba(ProGlu).2H$_2$O, 0.75 g) in 25 ml of water. The resulting solution was stirred at room temperature for 3 hours. After BaSO$_4$ precipitated was removed by filtering, the filtrate was freeze-dried, and the solid product was recrystallized from water and acetone, to obtain the desired product in 87% yield.

Composition: C$_{14}$H$_{25}$N$_3$O$_5$Pt.H$_2$O.

Elemental Analysis: C, 31.86; H, 5.12; N, 7.85; theoretical value: C, 31.82; H, 5.15; N, 7.95.

H-NMR spectrum (D$_2$O, ppm): 4.0 (m, 1H, Glu-CH), 2.3–2.1 (m, 6H, Pro-CH$_2$, dach-CH, Glu-CH$_2$), 2.0–1.7 (m, 4H, dach-CH, Glu-CH$_2$), 1.5–1.4 (m, 2H, dach-CH), 1.3–0.9 (m, 7H, dach-CH, Pro-CH$_3$).

Pt-NMR spectrum (D$_2$O, ppm): −1847.2.

IR absorption spectrum (KBr, cm$^{-1}$): 3231w, 3114w, 1629s, 1392m, 1310m.

Example 3

Preparation of (N-pivalyl-L-glutamato-O,O)(trans-(±)-1,2-diaminocyclo-hexane-N,N)platinum(II), [Pt(dach)(PivGlu)]

An aqueous solution of (trans-(±)-1,2-diaminocyclohexane-N,N)platinum(II) sulfate (Pt(dach) SO$_4$.H$_2$O, 0.42 g) in 20 ml of water was add to an aqueous solution of barium salt of N-pivalyl-L-glutamic acid (Ba (PivGlu).2H$_2$O, 0.40 g) in 20 ml of water. The resulting solution was stirred at room temperature for 3 hours. After BaSO$_4$ precipitated was removed by filtering, the filtrate was freeze-dried, and the solid product was recrystallized from water and acetone, to obtain the desired product in 90% yield.

Composition: C$_{16}$H$_{29}$N$_3$O$_5$Pt.2H$_2$O.

Elemental Analysis: C, 33.24; H, 5.68; N, 7.29; theoretical value: C, 33.45; H, 5.79; N, 7.31.

H-NMR spectrum (D$_2$O, ppm): 4.0 (m, 1H, Glu-CH), 2.3–2.1 (m, 4H, dach-CH$_2$, Glu-CH$_2$), 2.0–1.8 (m, 4H, dach-CH, Glu-CH$_2$), 1.5–1.4 (m, 2H, dach-CH), 1.3–1.0 (m, 13H, dach-CH, Piv-CH$_3$).

Pt-NMR spectrum (D$_2$O, ppm): −1861.4.

IR absorption spectrum (KBr, cm$^{-1}$): 3232w, 3103w, 1624s, 1513m, 1389m.

Example 4

Preparation of (N-carbobenzyloxy-L-glutamato-O, O)(trans-(±)-1,2-diamino cyclohexane-N,N)platinum (II), [Pt(dach)(CbzGlu)]

N-carbobenzyloxy-L-glutamic acid (0.28 g) and 1M aqueous sodium hydroxide (2 ml) were add to 10 ml of distilled water, and the resulting solution was stirred for 30 minutes. An aqueous solution of (trans-(±)-1,2-diaminocyclohexane-N,N)platinum(II) sulfate (Pt(dach) SO$_4$.H$_2$O, 0.42 g) in 20 ml of water was added to the above solution. The resulting solution was stirred for 4 hours at room temperature. The precipitate obtained was filtered and washed with water, ethanol and ethyl ether, and then vacuum-dried, to obtain the desired product in 80% yield.

Composition: C$_{19}$H$_{27}$N$_3$O$_6$Pt.2H$_2$O.

Elemental Analysis: C, 36.80; H, 4.91; N, 6.62; theoretical value: C, 36.54; H, 5.00; N, 6.73.

IR absorption spectrum (KBr, cm$^{-1}$): 3227w, 3119w, 1705m, 1623s, 1338s, 1344s, 1252m.

Example 5

Preparation of (N-phthaloyl-L-glutamato-O,O) (trans-(±)-1,2-diaminocyclo-hexane-N,N)platinum (II), [Pt(dach)(PhthGlu)]

The desired product was obtained in 83% yield using sodium salt of N-phthaloyl-L-glutamic acid as a starting material, in the same manner as described in the above Example 4.

Composition: C$_{19}$H$_{23}$N$_3$O$_6$Pt.H$_2$O.

Elemental Analysis: C, 38.02; H, 4.16; N, 6.87; theoretical value: C, 37.88; H, 4.18; N, 6.97.

IR absorption spectrum (KBr, cm$^{-1}$): 3215w, 3105w, 1709s, 1613s, 1390s, 1339s, 1171m, 1115m.

Example 6

Preparation of (N-tosyl-L-glutamato-O,O)(trans-(±)-1,2-diaminocyclo-hexane-N,N)platinum(II), [Pt(dach)(TsGlu)]

The desired product was obtained in 86% yield using barium salt of N-tosyl-L-glutamic acid as a starting material, in the same manner as described in the above Example 1.

Composition: C$_{18}$H$_{27}$N$_3$O$_6$Pt.2H$_2$O.

Elemental Analysis: C, 33.21; H, 4.72; N, 6.49; theoretical value: C, 33.54; H, 4.85; N, 6.52.

IR absorption spectrum (KBr, cm$^{-1}$): 3234w, 3119w, 1626s, 1374m, 1272m, 1156s, 1092m.

Example 7

Preparation of (N-acetyl-L-aspartato-O,O)(trans-(±)-1,2-diaminocyclo-hexane-N,N)platinum(II), [Pt(dach)(AcAsp)]

The desired product was obtained in 80% yield using barium salt of N-acetyl-L-aspartic acid as a starting material, in the same manner as described in the above Example 1.

Composition: C$_{12}$H$_{21}$N$_3$O$_5$Pt.2H$_2$O.

Elemental Analysis: C, 27.80; H, 4.86; N, 8.11; theoretical value: C, 27.88; H, 4.77; N, 8.10.

IR absorption spectrum (KBr, cm$^{-1}$): 3228w, 3101w, 1631s, 1546s, 1376s, 1293m.

Example 8

Preparation of (N-carbobenzyloxy-L-aspartato-O,O) (trans-(±)-1,2-diamino-cyclohexane-N,N)platinum (II), [Pt(dach)(CbzAsp)]

The desired product was obtained in 85% yield using barium salt of N-carbobenzyloxy-L-aspartic acid as a starting material, in the same manner as described in the above Example 1.

Composition: $C_{18}H_{25}N_3O_6Pt\cdot2H_2O$.

Elemental Analysis: C, 35.30; H, 4.64; N, 6.68; theoretical value: C, 35.41; H, 4.79; N, 6.88.

IR absorption spectrum (KBr, cm$^{-1}$): 3225w, 3120w, 1707s, 1632s, 1383m, 1333m.

Example 9

Preparation of (N-acetyl-L-aspartato-O,O)(2,2-dimethyl-1,3-propane-diamine-N,N)platinum(II), [Pt(dmpda)(AcAsp)]

The desired product was obtained in 80% yield using sodium salt of N-acetyl-L-aspartic acid and (2,2-dimethyl-1,3-propanediamine-N,N)platinum(II) sulfate as starting materials, in the same manner as described in the above Example 1.

Composition: $C_{11}H_{21}N_3O_5Pt\cdot H_2O$.

Elemental Analysis: C, 27.26; H, 4.65; N, 8.52; theoretical value: C, 27.05; H, 4.75; N, 8.60.

IR absorption spectrum (KBr, cm$^{-1}$): 3234w, 3129w, 1635s, 1550s, 1376m, 1289m.

Example 10

Bioassay for Antitumor Activity

Antitumor activities of the platinum complexes prepared in the above Examples 1 to 9 were assayed against the leukemia L1210 cell line according to the known method (S. S. Lee, O.-S. Jung, C. O. Lee, S. U. Choi, M.-J. Jun, Y. S. Sohn, *Inorg. Chim. Acta*, 239, 133 (1995)), and the results are shown in Table 1.

TABLE 1

| Compound | IC$_{50}$ ($\mu$M) | T/C (%)/dosage amount (mg/kg) |
|---|---|---|
| Pt(dach)(AcGlu) | 4.63 | 190.9/40, 227.3/20 |
| Pt(dach)(ProGlu) | 2.94 | 228.8/40, 212.5/20 |
| Pt(dach)(PivGlu) | 2.23 | 212.5/40, 211.3/20 |
| Pt(dach)(CbzGlu) | 65.08 | 207.5/40, 170.0/20 |
| Pt(dach)(PhthGlu) | 34.9 | 221.6/40, 177.3/20 |
| Pt(dach)(TsGlu) | 17.58 | 191.3/40, 176.3/20 |
| Pt(dach)(AcAsp) | 3.73 | 225.0/40, 179.6/20 |
| Pt(dach)(CbzAsp) | 26.46 | 193.8/40, 175.0/20 |
| Pt(dmpda)(AcAsp) | 3.19 | 160.4/40, 146.2/20 |
| Cisplatin | 1 | 184/4 |
| Carboplatin | 10.24 | 168/40 |

\* dach: trans-(±)-1,2-diaminocyclohexane,
dmpda: 2,2-dimethyl-1,3-propanediamine,
Ac: acetyl,
Pro: propionyl,
Piv: pivalyl,
Cbz: carbobenzyloxy,
Phth: phthalyl,
Ts: tosyl,
Glu: L-glutamato,
Asp: L-aspartato As described above, in the platinum (II) complex of N-substituted amino dicarboxylate of the present invention, a lipophilic substituent was introduced on the N-position of the amino dicarboxylate, and therefore, hydrophilicity of the platinum complex is lowered to some degree, but its lipophilicity was improved. Therefore, the present complexes can be formulated with a lipophilic drug delivery material such as liposome, so that their bioavailability can be greatly improved.

As can be seen from Table 1, the platinum complexes of N-substituted amino dicarboxylates of the present invention exhibited superior antitumor activities compared to cisplatin or carboplatin which are presently in clinical use. Therefore, the platinum complexes of the present invention are in great potential to be used as an anti-tumor agent with or without formulation using a drug delivery material such as liposome.

Furthermore, unlike the conventional method in which a platinum complex is prepared using an unsubstituted amino dicarboxylate, the platinum complexes prepared from the N-substituted amino dicarboxylate according to the present invention do not undergo a linkage isomerism in aqueous solution. Accordingly, it is possible to selectively prepare pure (O,O)-linked platinum(II) complexes which show excellent antitumor activity.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A platinum(II) complex of N-substituted amino dicarboxylate represented by the following formula (1):

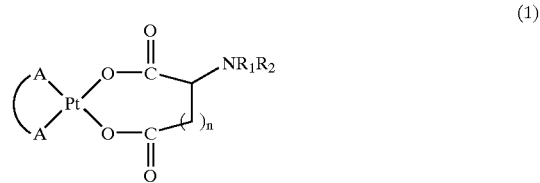

(1)

wherein n is 1 or 2;

A—A is a diamine selected from the group consisting of trans-(±)-1,2-diaminocyclohexane, ethylenediamine and 2,2-dimethyl-1,3-propanediamine; and R$_1$ is hydrogen and R$_2$ is RCO or RSO$_2$, wherein R is an alkyl selected from the group consisting of methyl, ethyl, n-propyl, n-butyl and t-butyl or an aryl selected from the group consisting of phenyl and substituted phenyl group, or R$_1$R$_2$ is phthaloyl.

2. A preparation method of a platinum(II) complex of N-substituted amino dicarboxylate represented by the formula (1) comprising a step of reacting a salt of N-substituted amino dicarboxylate with a platinum (II) sulfate complex represented by the following formula (3):

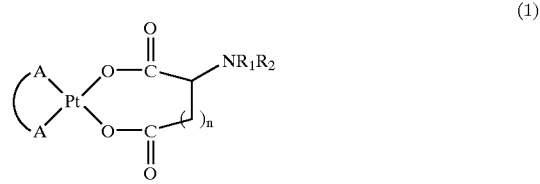

(1)

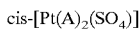

(3)

wherein n is 1 or 2;

A—A is a diamine selected from the group consisting of trans-(±)-1,2-diaminocyclohexane, ethylenediamine and 2,2-dimethyl-1,3-propanediamine; and R$_1$ is hydrogen and R$_2$ is RCO or RSO$_2$, wherein R is an alkyl selected from the group consisting of methyl, ethyl, n-propyl, n-butyl and t-butyl or an aryl selected from the group consisting of phenyl and substituted phenyl group, or $R_1R_2$ is phthaloyl.

3. The method according to claim 2, wherein the salt of N-substituted amino dicarboxylate is a salt represented by the following chemical formula (2) or (4):

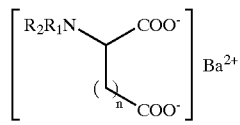

(2)

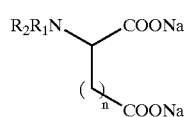

(4)

wherein n is 1 or 2;

A—A is a diamine selected from the group consisting of trans-(±)-1,2-diaminocyclohexane, ethylenediamine and 2,2-dimethyl-1,3-propanediamine; and $R_1$ is hydrogen and $R_2$ is RCO or $RSO_2$, wherein R is an alkyl selected from the group consisting of methyl, ethyl, n-propyl, n-butyl and t-butyl or an aryl selected from the group consisting of phenyl and substituted phenyl group, or $R_1R_2$ is phthaloyl.

4. The method according to claim 2, wherein molar ratio of the salt of N-substituted amino dicarboxylate to the platinum (II) sulfate complex is 1.0:1.0–1.3.

5. The method according to claim 2, wherein the reaction is performed at room temperature.

6. The method according to claim 2, wherein the reaction medium is water.

* * * * *